US005690919A

United States Patent [19]

Röckl et al.

[11] Patent Number: 5,690,919

[45] Date of Patent: Nov. 25, 1997

[54] DEODORIZING COSMETIC COMPOSITIONS

[75] Inventors: Manfred Röckl, Wedel/Holst.; Bernd Traupe, Hamburg; Manfred Klier, Aumühle; Florian Wolf, Hamburg, all of Germany

[73] Assignee: Beiersdorf Aktiengesellschaft, Hamburg, Germany

[21] Appl. No.: 513,703

[22] Filed: Aug. 11, 1995

[30] Foreign Application Priority Data

Aug. 19, 1994 [DE] Germany .......................... 44 29 467.0

[51] Int. Cl.$^6$ ............................ A61K 7/32; A61K 31/19; A61K 31/20

[52] U.S. Cl. ............................ 424/65; 514/553; 514/557; 514/558

[58] Field of Search ............................ 424/65; 514/553, 514/557, 558

[56] References Cited

U.S. PATENT DOCUMENTS 4,425,321 1/1984 Jacquet et al. ............................ 424/47

*Primary Examiner*—Shelley A. Dodson
*Attorney, Agent, or Firm*—Sprung Kramer Schaefer & Briscoe

[57] ABSTRACT

Use of a mixture of (a) dodecanoic acid (lauric acid)

(b) at least one other fatty acid, selected from the group of unbranched saturated fatty acids having a chain length of $C_{6-20}$, at least one of the other fatty acids having to have a chain length of greater than $C_{12}$, (c) glyceryl monocaprylate and/or glyceryl monocaprate (d) with omission of ethoxylated glyceryl fatty acid esters and propoxylated glyceryl fatty acid esters (e) in the pH range below 8 as active principle for the selective reduction of coryneform bacteria or as a deodorant active compound.

22 Claims, No Drawings

DEODORIZING COSMETIC COMPOSITIONS

The present invention relates to cosmetic deodorants. Such formulations are used to eliminate body odour which is formed if fresh perspiration, which is odourless per se, is decomposed by microorganisms. The customary cosmetic deodorants are based on various principles of action.

Deodorants which are known and customary are both liquid deodorants, for example aerosol sprays, roll-ons and the like and also solid preparations, for example deodorant sticks, powders, powder sprays, intimate cleansing agents, etc.

In so-called antiperspirants, the formation of perspiration can be suppressed by astringents, mainly aluminium salts, such as aluminium hydroxychloride (aluminiumchlorohydrate). Apart from the denaturation of the skin proteins, the substances used for this purpose, however, depending on their dosage, drastically intervene in the heat balance of the axillary region and should at best be used in exceptional cases.

The bacterial flora on the skin can be reduced by the use of antimicrobial substances in cosmetic deodorants. In the ideal case, only the odour-causing micro-organisms should be effectively reduced here. In practice, however, it has emerged that all the microflora of the skin can be harmed.

The flow of perspiration itself is not affected by this, and in the ideal case only the microbial decomposition of the perspiration is temporarily stopped.

The combination of astringents with antimicrobially active substances in one and the same composition is also customary. The disadvantages of both classes of active compound, however, cannot be completely eliminated in this way.

Finally, body odour can also be masked by fragrances, a method which least meets the aesthetic requirements of the consumer, as the mixture-of body odour and perfume fragrance smells rather unpleasant.

Nevertheless, most cosmetic deodorants, and indeed the majority of cosmetics overall, are perfumed, even if they comprise deodorizing active compounds. Perfuming can also serve to increase the consumer acceptance of a cosmetic product or to give a product a certain flair.

The perfuming of cosmetic compositions, in particular cosmetic deodorants, containing active compounds is, nevertheless, sometimes problematic, because active compounds and perfume constituents occasionally react with one another and can render each other inactive.

Deodorants should fulfil the following conditions:

1) They should effect reliable deodorizing.
2) The natural biological processes of the skin must not be impaired by the deodorants.
3) The deodorants must be harmless in the case of overdosage or other unintended use.
4) They should not become concentrated on the skin after repeated use.
5) They should he easily incorporated into customary cosmetic formulations.

The object of the present invention was thus to develop cosmetic deodorants which do not have the disadvantages of the prior art. In particular, the deodorants should largely preserve the microflora of the skin, but selectively reduce the number of microorganisms which are responsible for body odour.

It was furthermore an object of the invention to develop cosmetic deodorants which are distinguished by good skin tolerability. In no case should the deodorizing active principles become concentrated on the skin.

Another object was to develop cosmetic deodorants which harmonize with as large a number as possible of customary cosmetic auxiliaries and additives, in particular with the perfume constituents which are precisely of importance in formulations having a deodorizing or antiperspirant action.

Yet another object of the invention was to make available cosmetic deodorants which are active over a relatively long period of time, to be specific in the order of at least half a day, without their action noticeably falling off.

Finally, an object of the present invention was to develop deodorizing cosmetic principles which can be incorporated as universally as possible into all sorts of presentation forms of cosmetic deodorants, without being restricted to one or a few specific presentation forms.

It has surprisingly been found, and therein lies the achievement of all these objects, that the use of a mixture of (a) dodecanoic acid (lauric acid)
(b) at least one other fatty acid, selected from the group of unbranched saturated fatty acids having a chain length of $C_{6-20}$, at least one of the other fatty acids having to have a chain length of greater than $C_{12}$,
(c) glyceryl monocaprylate and/or glyceryl monocaprate
(d) with omission of ethoxylated glyceryl fatty acid esters and propoxylated glyceryl fatty acid esters
(e) in the pH range below 8 as active principle for the selective reduction of coryneform bacteria, or the use of a mixture of (a) dodecanoic acid (lauric acid)
(b) at least one other fatty acid, selected from the group of unbranched saturated fatty acids having a chain length of $C_{6-20}$, at least one of the other fatty acids having to have a chain length of greater than $C_{12}$,
(c) glyceryl monocaprylate and/or glyceryl monocaprate
(d) with omission of ethoxylated glyceryl fatty acid esters and propoxylated glyceryl fatty acid esters
(e) in the pH range below 8 as a deodorant active compound remedies the disadvantages of the prior art.

In addition, the mixture of (a) lauric acid and (b) at least one other fatty acid inherent in the invention is occasionally designated for the sake of simplicity as the "fatty acid mixture according to the invention" or provided with similar designations.

Although according to the invention all five conditions from (a) to (e) must be fulfilled, the constituents (a) and (b) are occasionally combined for practical reasons. In a particular embodiment of the present invention, especially if (a) and (b) can be taken from a specific fatty acid fraction, they namely, as it were, form one unit.

EP Offenlegungsschrift 0 243 145 indeed discloses an antimicrobially active topical pharmaceutical composition which, according to the independent Claims 2 and 3, is a ternary mixture of a glyceryl fatty acid ester, and/or an ethoxylated glyceryl fatty acid ester and/or a propoxylated glyceryl fatty acid ester, a mixture of fatty acids and a pharmaceutically acceptable excipient, the fatty acids consisting of a first fatty acid having a chain length of $C_{6-18}$ and a second fatty acid having a chain length of $C_{6-18}$.

Dodecanoic acid and other fatty acids according to the invention are indeed formally included by these generic fatty acid formulae. The antimicrobial action described in this specification, however, is ascribed solely to the action of the glyceryl fatty acid esters, the ethoxylated glyceryl fatty acid esters and/or the propoxylated glyceryl fatty acid esters, on which all compositions described there are necessarily based.

This specification takes a different direction than that given by the present invention. In fact, it has surprisingly been found that addition of glyceryl fatty acid esters, ethoxylated glyceryl fatty acid esters and/or propoxylated glyceryl fatty acid esters considerably reduces the antimicrobial action of the-mixture according to the invention of lauric acid and other fatty acids, and in some cases even abolishes it entirely at certain concentrations.

This is true for all glyceryl fatty acid esters, apart from glyceryl monocaprylate and glyceryl monocaprate. These two glyceryl esters are indeed mentioned in EP Offenlegungsschrift 0 243 145. This specification, however, only discloses pharmaceuticals, the point of their application precisely not being selectively to destroy the microorganisms producing body odour, but to combat a plurality of microorganisms. For body deodorants, EP Offenlegungsschrift 0 243 145 thus leads the person skilled in the art of body deodorants astray in two respects.

EP Offenlegungsschrift 0 465 423 describes a pharmaceutical composition for the control of microorganisms, which essentially comprises an inert carrier and an active constituent which consists of an effective amount of one or more compounds selected from fatty acids having a chain length from $C_{4-14}$ and their monoglycerides, and of mono- or polyunsaturated fatty acids having a chain length of $C_{14-22}$ and their monoglycerides. This specification likewise discloses only pharmaceuticals and not cosmetics. This specification also contains no indications in the direction of the present invention.

Finally, it is known to employ soaps, i.e. salts of the acids according to the invention, in combination. However, these are not active according to the invention. Surprisingly, the mixtures according to the invention display their advantageous antimicrobial and deodorizing cosmetic action only in the pH range below 8.

The deodorizing action of the mixtures according to the invention is based primarily on their selective toxicity for Gram-positive, in particular coryneform, bacteria. These are regarded as the microorganisms mainly responsible for the decomposition of apocrine perspiration. As these mixtures at the same time are completely harmless to humans and other warm-blooded animals, they are ideally suitable for use in cosmetic deodorants.

In particular, it was surprising that although lauric acid, which in general is the main constituent of the mixtures according to the invention, is estimated as being slightly skin-irritating in very sensitive persons, the mixtures according to the invention, however, never showed even the slightest symptoms of irritation in subjects with sensitive skin.

It was further surprising that the mixtures according to the invention act in a synergistic manner against coryneform bacteria.

In "Antiseptica" (Antiseptics), part 3, sub-title "Antibakterielle, antifungielle und antivirale Antiseptik-ausgewählte Wirkstoffe" [Antibacterial, antifungal and antiviral antiseptics—selected active compounds], Gustav Fischer Verlag, Stuttgart, New York, 1987, pp. 250 ff. it is shown that although lauric acid is highly active against coryneform bacteria, the other $C_{6-20}$-fatty acids, however, at best produce a weak action.

In the place indicated it is further mentioned that some of the fatty acids to be employed according to the invention have certain microbicidal properties. Nothing was known hitherto about a synergistic interplay of the individual fatty acid components with one another and with glycerol monocaprate and/or glycerol monocaprylate.

Glyceryl monocaprylate and glyceryl monocaprate are characterized by the general formula

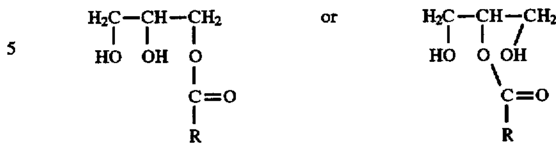

where R can represent the heptanyl radical and/or nonanyl radical.

In this specification, in particular in the examples, the abbreviation GMCy is used for glycerol monocaprylate and the abbreviation GMC for glycerol monocaprate.

In the glycerol esters esterified in the 1-position of the glycerol, the 2-position is a centre of asymmetry. The 2S- and the 2R-configuration are active according to the invention and equally advantageous.

It has emerged as being favourable to use racemic mixtures of the stereoisomers.

In the final formulations, i.e. the deodorizing cosmetics, the content of GMCy and/or GMC is advantageously 0.1–10.0% by weight, preferably 0.5 to 7.5% by weight, particularly preferably 1.5–5.0% by weight, in each case relative to the total weight of the particular formulation.

Preferably, the $C_{6-20}$-fatty acids are selected from the group consisting of caproic acid (hexanoic acid), caprylic acid (octanoic acid), pelargonic acid (nonanoic acid), capric acid (decanoic acid), myristic acid (tetradecanoic acid), palmitic acid (hexadecanoic acid) and stearic acid (octadecanoic acid).

It is advantageous to choose the following weight ratios, independently of whether a mixture of lauric acid with one or more other fatty acids is present:

| | |
|---|---|
| Lauric acid:caproic acid | = 50:0 to 50:5 and/or |
| Lauric acid:caprylic acid | = 50:1 to 50:20 and/or |
| Lauric acid:pelargonic acid | = 50:1 to 50:20 and/or |
| Lauric acid:capric acid | = 50:1 to 50:20 and/or |
| Lauric acid:myristic acid | = 50:5 to 50:30 and/or |
| Lauric acid:stearic acid | = 50:1 to 50:50. |

It is particularly advantageous to choose the following weight ratios:

| | |
|---|---|
| Lauric acid:caproic acid | = 50:0 to 50:1 and/or |
| Lauric acid:caprylic acid | = 50:2 to 50:15 and/or |
| Lauric acid:pelargonic acid | = 50:2 to 50:15 and/or |
| Lauric acid:capric acid | = 50:2 to 50:15 and/or |
| Lauric acid:myristic acid | = 50:10 to 50:20 and/or |
| Lauric acid:stearic acid | = 50:2 to 50:20. |

If lauric acid is present in a mixture with several other fatty acids, it is furthermore favourable to use a mixture of lauric acid, capric acid and caprylic acid, especially if the weight ratio is selected from the range Lauric acid: caprylic acid: capric acid=50:1:1 to 50:20:20.

Preferably, the weight ratio is then chosen from the range

Lauric acid: caprylic acid: capric acid=50:1:1 to 50:5:5.

The use of caproic acid is indeed thoroughly advantageous according to the invention and leads per se to mixtures having good action against coryneform bacteria. Because of the unpleasant intrinsic smell of caproic acid, however, this concentration should be kept low.

The preferred embodiment of the present invention consists in choosing the ratio of lauric acid to one or alternatively several of the other fatty acids according to the invention such that it corresponds to the ratio in a hydrogenated (hardened) cut of fatty acids from natural coconut fatty acid mixture.

The composition of the natural coconut fatty acids is approximately:

| | |
|---|---|
| Lauric acid: | 44–51% by weight |
| Myristic acid: | 13–18% by weight |
| Palmitic acid: | 8–10% by weight |
| Caprylic acid: | 6–9% by weight |
| Capric acid: | 6–10% by weight |
| Oleic acid: | 5–8% by weight |
| Stearic acid: | 1–3% by weight |
| Linoleic acid: | 0–2% by weight |
| Caproic acid: | 0–1% by weight |

The composition of the hardened (hydrogenated) coconut fatty acids is approximately.

| | |
|---|---|
| Lauric acid: | 44–51% by weight |
| Myristic acid: | 13–18% by weight |
| Palmitic acid: | 8–10% by weight |
| Caprylic acid: | 6–9% by weight |
| Capric acid: | 6–10% by weight |
| Stearic acid: | 6–13% by weight |
| Caproic acid: | 0–1% by weight |

Lauric acid (CAS No. 143-07-7) is available from various suppliers, for example from Aarhus Oliefabrik A/S, from the Aceto Chemical Company Inc., from Dansk Sojakagefabrik A/S, from Procter & Gamble Ltd. and others.

Hydrogenated coconut fatty acid is available under the commercial name Hydrofol® Acid 631 from Ashland Chemical Company and under the name Edenor® HK 8-18 from Henkel KGaA.

The following composition of the fatty acid mixtures according to the invention is preferred:

| | |
|---|---|
| Lauric acid: | 1–99% by weight |
| Myristic acid: | 0–18% by weight |
| Palmitic acid: | 0–10% by weight |
| Caprylic acid: | 0–9% by weight |
| Capric acid: | 0–10% by weight |
| Stearic acid: | 1–99% by weight |
| Caproic acid: | 0–1% by weight |

in each case relative to the total weight of the fatty acid mixture.

Particularly advantageous compositions are obtained if the composition of the fatty acid mixture according to the invention is chosen as follows:

| | |
|---|---|
| Lauric acid: | 10–90% by weight |
| Myristic acid: | 13–18% by weight |
| Palmitic acid: | 8–10% by weight |
| Caprylic acid: | 6–9% by weight |
| Capric acid: | 6–10% by weight |
| Stearic acid: | 10–90% by weight |
| Caproic acid: | 0–1% by weight |

in each case relative to the total weight of the fatty acid mixture.

In particular, advantageous compositions are obtained if the composition of the fatty acid mixture according to the invention is chosen as follows:

| | |
|---|---|
| Lauric acid: | 44–51% by weight |
| Myristic acid: | 13–18% by weight |
| Palmitic acid: | 8–10% by weight |
| Caprylic acid: | 6–9% by weight |
| Capric acid: | 6–10% by weight |
| Stearic acid: | 6–13% by weight |
| Caproic acid: | 0–1% by weight, |

in each case relative to the total weight of the fatty acid mixture.

According to the specification, Edenor® HK 8-18 is distinguished by the following approximate content of the fatty acids according to the invention:

| | |
|---|---|
| Lauric acid: | 48% by weight |
| Myristic acid: | 18% by weight |
| Palmitic acid: | 8% by weight |
| Caprylic acid: | 7% by weight |
| Capric acid: | 7% by weight |
| Stearic acid: | 10% by weight |
| Caproic acid: | 1% by weight |

in each case relative to the total weight of the mixture.

The use of this commercial product is advantageous. In the final formulations, i.e. the deodorizing cosmetics, the content of the fatty acid mixtures according to the invention is advantageously 0.1–10.0% by weight, preferably 0.5 to 7.5% by weight, particularly preferably 1.5–5.0% by weight, in each case relative to the total weight of the respective formulation.

The ratio of GMCy and/or GMC to one another on the one hand and the fatty acid mixture on the other hand can be advantageously chosen from the range 20:1 to 1:20, preferably from the range 5:1 to 1:5.

The cosmetic deodorants according to the invention can be present in the form of aerosols, i.e. preparations which can be sprayed from aerosol containers, squeeze bottles or by a pump device, or in the form of liquid compositions which can be applied by means of roll-on devices, but also in the form of W/O or O/W emulsions, e.g. creams or lotions, which can be applied from normal bottles and containers. The cosmetic deodorants furthermore can advantageously be present in the form of deodorizing tinctures, deodorizing intimate cleansing agents, deodorizing shampoos, deodorizing shower or bath preparations, deodorizing powders or deodorizing powder sprays.

In general, deodorizing gel sticks (deodorant sticks) are not a suitable presentation form for the mixtures according to the invention, as they usually have a high pH. In a basic medium, however, the fatty acid mixtures according to the invention are converted to the corresponding soaps, which are not, or not adequately, antimicrobially active.

In contrast, deodorizing sticks which have a pH of less than 8 are thoroughly advantageous presentation forms.

Customary cosmetic carriers which can be employed for the preparation of the deodorizing compositions according to the invention, in addition to water, ethanol and isopropanol, glycerol and propylene glycol, are skin care fatty or fat-like substances, such as decyl oleate, cetyl alcohol, cetylstearyl alcohol and 2-octyldodecanol, in the quantitative ratios customary for such preparations, and mucigenous substances and thickening agents, e.g. hydroxyethyl- or hydroxypropylcellulose, polyacrylic acid and polyvinylpyrrolidone, but in addition, in small amounts, also cyclic silicone oils (polydimethylsiloxanes) and liquid polymethylphenylsiloxanes of low viscosity.

Suitable propellants for cosmetic deodorants according to the invention which can be sprayed from aerosol containers are the customary known readily volatile liquefied propellants, for example hydrocarbons (propane, butane and isobutane), which can be employed on their own or as a mixture with one another. Compressed air can also be advantageously used.

The person skilled in the art of course knows that there are non-toxic propellants which would be fundamentally suitable for the present invention, but which nevertheless should be omitted because of a questionable action on the environment or other accompanying circumstances, in particular chlorofluorohydrocarbons (CFCs).

Emulsifiers which have proved suitable for the preparation of the cosmetic deodorants according to the invention which are advantageously to be applied to the desired areas of skin as liquid preparations by means of a roll-on device, and which can be used in the compositions in a small amount, e.g. 2 to 5% by weight, relative to the total composition, are non-ionic types, such as polyoxyethylene fatty alcohol ethers, e.g. cetostearyl alcohol polyethylene glycol ethers having 12 to 20 ethylene oxide units added per molecule, cetostearyl alcohol as well as sorbitan ester and sorbitan ester/ethylene oxide compounds (e.g. sorbitan monostearate and polyoxyethylenesorbitan monostearate) and long-chain higher molecular weight waxy polyglycol ethers.

In addition to the constituents mentioned, perfume, colorants, antioxidants (e.g. alpha-tocopherol and its derivatives or butylated hydroxytoluene (BHT=2,6-di-tert-butyl-4-methylphenol) in amounts from 0.01 to 0.03%, relative to the total composition), suspending agents, buffer mixtures or other customary cosmetic bases can be admixed to the deodorizing cosmetic agents according to the invention, whose pH is preferably adjusted, e.g. by customary buffer mixtures, to 4.0 to 7.5, in particular 5.0 to 6.5.

It is essential for the present invention that the pH of the cosmetic deodorants according to the invention is less than 8. pHs which are slightly higher than 7, but less than 7.5, can in general be tolerated here. At any rate, it is easy to determine what exact upper pH limit is to be observed for a given fatty acid mixture in an individual case by simple trial and error, without inventive activity.

The lower pH limit is determined solely by dermatological conditions. As cosmetics and dermatologicals should not have a pH of less than approximately 3.5–4, this range can be regarded as the lower limit. Nevertheless, the compositions according to the invention are fundamentally also active at even lower pHs.

The pH of the formulations according to the invention is advantageously adjusted to the acid to very weakly alkaline range of less than 8, preferably from 4.0–7.5, particularly preferably from 5.0–6.5.

The amounts of cosmetic carriers and perfume to be employed in each case can easily be determined by the person skilled in the art by simple trial and error depending on the nature of the particular product.

For perfuming, optionally those substances and perfume oils are also suitable which are stable, do not irritate the skin and as such already have antibacterial or bacteriostatic properties.

The preparation of the cosmetic compositions is usually carried out in the customary manner, apart from special preparations which are noted separately in each case in the examples, by simple mixing while stirring, optionally with gentle warming. It presents no difficulties. For emulsions, the fatty phase and the water phase are prepared separately, for example, if appropriate with heating, and then emulsified.

Otherwise the customary rules for making up cosmetic formulations, which are familiar to the person skilled in the art, are to be observed.

If the combinations according to the invention are to be incorporated into powder sprays, the suspension bases for this can advantageously be chosen from the group consisting of silica gels (e.g. those which are obtainable under the trade name Aerosil®) kieselguhr, talc, modified starch, titanium dioxide, silk powder, nylon powder, polyethylene powder and related substances.

Advantageous exemplary embodiments of the present invention follow.

EXAMPLE 1

Aerosol spray I
(a) Liquid phase

| | % by weight |
|---|---|
| Octyldodecanol | 0.50 |
| Coconut fatty acid cut (containing | 0.50 |
| caproic acid | 1% |
| caprylic acid | 7% |
| capric acid | 6% |
| lauric acid | 48% |
| myristic acid | 19% |
| stearic acid | 10%) |
| Perfume | q.s. |
| Ethyl alcohol | to 100.00 |

(b) The liquid phase obtained under (a) is introduced into aerosol containers together with a propane/butane 2.7 mixture in the ratio 39:61.

EXAMPLE 2

Aerosol spray II
(a) Liquid phase

| | % by weight |
|---|---|
| Octyldodecanol | 0.50 |
| Coconut fatty acid cut (see Example 1) | 0.20 |
| Perfume | q.s. |
| Isopropyl alcohol | to 100.00 |

(b) The liquid phase obtained under (a) is introduced into aerosol containers together with a propane/butane 2.7 mixture in a ratio of 39:61.

EXAMPLE 3

Pump spray I

| | % by weight |
|---|---|
| (a) | |
| Ethyl alcohol | 60.00 |
| Glycerol | 1.00 |
| PEG 40/hydrogenated castor oil | 2.00 |
| Coconut fatty acid cut (see Example 1) | 0.50 |
| Perfume | g.s. |
| (b) | to100.00 |
| Water | |

The constituents mentioned under (a) are processed to give a homogeneous solution, then slowly made up with the water phase (b). The finished pump spray can then be introduced into pump atomizers.

EXAMPLE 4

Roll-on gel I

| | % by weight |
|---|---|
| (a) | |
| 1,3-Butylene glycol | 2.00 |
| Hydroxyethycellulose (e.g. Tylose 4000, Hoechst) | 0.50 |
| (b) Water | to100.00 |
| (c) | |
| Ethyl alcohol | 60.00 |
| PEG 40/hydrogenated castor oil | 2.00 |
| Coconut fatty acid cut (see Example 1) | 0.30 |
| Perfume | q.s. |

The constituents mentioned under (a) are dispersed, water (b) is added, the mixture is left to swell at room temperature, and a solution of the constituents mentioned under (c) is added after about 15 minutes. The resulting mixture is homogenized and can be transferred to containers.

EXAMPLE 5

Wax stick I

| | % by weight |
|---|---|
| Hydrogenated castor oil | 5.00 |
| Beeswax | 6.00 |
| Ceresin (hard ozocerite) | 30.00 |
| $C_{12-15}$-alcohol benzoates | 17.00 |
| Coconut fatty acid cut (see Example 1) | 0.40 |
| Perfume | q.s. |
| Octyldodecanol | to100.00 |

The constituents are melted at about 75° C., well mixed and poured into suitable moulds.

EXAMPLE 6

Roll-on emulsion I

| | % by weight |
|---|---|
| (a) | |
| Triceteareth phosphate | 0.30 |
| Octyldodecanol | 2.00 |
| $C_{12-15}$-alcohol benzoates | 2.00 |
| Coconut fatty acid cut (see Example 1) | 0.50 |
| $C_{10-30}$-alkyl acrylates | 0.15 |
| (b) | |
| Water | to100.00 |
| NaOH | 0.05 |
| (c) | |
| Ethyl alcohol | 10.00 |
| Perfume | q.s. |

The constituents mentioned under (a) and (b) are in each case warmed to 75° C., with stirring. The constituents (a) are then added to (b). The mixture is cooled to 35° C. A solution is prepared from the constituents (c), which is then warmed to 35° C. and added with stirring to the mixture of (a) and (b).

EXAMPLE 7

Aerosol spray IV (a) Liquid phase

| | % by weight |
|---|---|
| Octyldodecanol | 0.50 |
| Fatty acid mixture (see Example 7) | 0.20 |
| Perfume | q.s. |
| Isopropyl alcohol | to100.00 |

(b) The liquid phase obtained under (a) is transferred together with a propane/butane 2.7 mixture in the ratio 39:61.

EXAMPLE 8

Pump spray II

| | % by weight |
|---|---|
| (a) | |
| Ethyl alcohol | 60.00 |
| Glycerol | 1.00 |
| PEG 40-hydrogenated castor oil | 2.00 |
| Fatty acid mixture (see Example 7) | 0.50 |
| Perfume | g.s. |
| (b) Water | to100.00 |

The constituents mentioned under (a) are processed to give a homogeneous solution, then slowly made up using the water phase (b). The finished pump spray can then be transferred to pump atomizers.

EXAMPLE 9

Roll-on gel II

| | % by weight |
|---|---|
| (a) | |
| 1,3-Butylene glycol | 2.00 |
| Hydroxyethylcellulose (e.g. Tylose 4000, Hoechst) | 0.50 |
| (b) Water | to100.00 |
| (c) | |
| Ethyl alcohol | 60.00 |
| PEG 40/hydrogenated castor oil | 2.00 |
| Fatty acid cut (see Example 7) | 0.30 |
| Perfume | q.s. |

The constituents mentioned under (a) are dispersed, water (b) is added, the mixture is allowed to swell at room temperature, and a solution of the constituents mentioned under (c) is added after about 15 minutes. The resulting mixture is homogenized and can be transferred to containers.

EXAMPLE 10

Wax stick II

| | % by weight |
|---|---|
| Hydrogenated castor oil | 5.00 |
| Beeswax | 6.00 |
| Ceresin (hard ozocerite) | 30.00 |
| $C_{12-15}$-alcohol benzoates | 17.00 |
| Fatty acid mixture (see Example 7) | 0.40 |
| Perfume | q.s. |
| Octyldodecanol | to100.00 |

The constituents are melted at about 75° C., well mixed and poured into suitable moulds.

EXAMPLE 11

Roll-on emulsion II

| | % by weight |
|---|---|
| (a) | |
| Triceteareth phosphate | 0.30 |
| Octyldodecanol | 2.00 |
| $C_{12-15}$-alcohol benzoates | 2.00 |
| Fatty acid mixture (see Example 7) | 0.50 |
| $C_{10-30}$-alkyl acrylates | 0.15 |
| (b) | |
| Water | to100.00 |
| NaOH | 0.05 |
| (c) | |
| Ethyl alcohol | 10.00 |
| Perfume | q.s. |

The constituents mentioned under (a) and (b) are in each case heated to 75° C., with stirring. The constituents (a) are then added to (b). The mixture is cooled to 35° C. A solution is prepared from the constituents (c), which is warmed to 35° C. and added with stirring to the mixture of (a) and (b).

EXAMPLE 12

Pump spray III

| | % by weight |
|---|---|
| (a) | |
| Ethyl alcohol | 60.00 |
| Glycerol | 1.00 |
| PEG 40/hydrogenated castor oil | 2.00 |
| Fatty acid mixture (see Example 7) | 0.50 |
| Perfume | q.s. |
| (b) | to100.00 |
| Water | |

The constituents mentioned under (a) are processed to give a homogeneous solution, and then slowly made up using the water phase (b). The finished pump spray can then be transferred to pump atomizers.

EXAMPLE 13

Roll-on gel III

| | % by weight |
|---|---|
| (a) | |
| 1,3-Butylene glycol | 2.00 |
| Hydroxyethylcellulose | 0.50 |
| (for example Tylose 4000, Hoechst) | |
| (b) | to100.00 |
| Water | |
| (c) | |
| Ethyl alcohol | 60.00 |
| PEG 40/hydrogenated castor oil | 2.00 |
| Fatty acid cut (see Example 7) | 0.30 |
| Perfume | q.s. |

The constituents mentioned under (a) are dispersed, water (b) is added, the mixture is allowed to swell at room temperature, and a solution of the constituents mentioned under (c) is added after about 15 minutes. The resulting mixture is homogenized and can then be transferred to containers.

EXAMPLE 14

Wax stick III

| | % by weight |
|---|---|
| Hydrogenated castor oil | 5.00 |
| Beeswax | 6.00 |
| Ceresin (hard ozocerite) | 30.00 |
| $C_{12-15}$-alcohol benzoates | 17.00 |
| Fatty acid mixture (see Example 7) | 0.40 |
| Perfume | q.s. |
| Octyldodecanol | to100.00 |

The constituents are melted at 75° C., well mixed and poured into suitable moulds.

EXAMPLE 15

Roll-on emulsion III

| | % by weight |
|---|---|
| (a) | |
| Triceteareth phosphate | 0.30 |
| Octyldodecanol | 2.00 |
| $C_{12-15}$-alcohol benzoates | 2.00 |
| Fatty acid mixture (see Example 7) | 0.50 |
| $C_{10-30}$-alkyl acrylates | 0.15 |
| (b) | |
| Water | to100.00 |
| NaOH | 0.05 |
| (c) | |
| Ethyl alcohol | 10.00 |
| Perfume | q.s. |

The constituents mentioned under (a) and (b) are in each case heated to 75° C. with stirring. The constituents (a) are then added to (b). The mixture is cooled to 35° C. A solution is prepared from the constituents (c), which is warmed to 35° C. and added with stirring to the mixture of (a) and (b).

We claim:

1. A process for selectively reducing coryneform bacteria comprising applying to the bacteria a mixture comprising a selectively reducing effective amount of (a) dodecanoic acid (lauric acid)

(b) at least one other fatty acid, selected from the group of unbranched saturated fatty acids having a chain length of $C_{6-20}$, at least one of the other fatty acids having to have a chain length of greater than $C_{12}$, (c) at least one of glyceryl monocaprylate or glyceryl monocaprate (d) with omission of ethoxylated glyceryl fatty acid esters and propoxylated glyceryl fatty acid esters wherein the pH of said mixture is below 8, said mixture being an active principle for selectively reducing coryneform bacteria.

2. A process according to claim 1, wherein the other fatty acids (b) are chosen from the group consisting of capric acid (hexanoic acid), caprylic acid (octanoic acid), pelargonic acid (nonanoic acid), capric acid (decanoic acid), myristic acid (tetradecanoic acid), palmitic acid (hexadecanoic acid) and stearic acid (octadecanoic acid).

3. A process according to claim 1, wherein at least one of the following weight ratios between lauric acid and at least one other fatty acid are chosen, independently of whether more other fatty acids are present, from the group consisting of:

| | | |
|---|---|---|
| Lauric acid:caproic acid | = | 50:0 to 50:5, |
| Lauric acid:caprylic acid | = | 50:1 to 50:20, |
| Lauric acid:pelargonic acid | = | 50:1 to 50:20, |
| Lauric acid:capric acid | = | 50:1 to 50:20, |
| Lauric acid:myristic acid | = | 50:5 to 50:30 or |
| Lauric acid:stearic acid | = | 50:1 to 50:50, |

wherein if the other fatty acid is solely caproic acid and is not caprylic acid, pelargonic acid, capric acid, myristic acid or stearic acid, then the amount of caproic acid in the ratio is greater than zero.

4. A process according to claim 1, wherein at least one of the following weight ratios are chosen between lauric acid and at least one of the following other fatty acids, independently of whether more other fatty acids are present, from the group consisting of:

| | | |
|---|---|---|
| Lauric acid:caproic acid | = | 50:0 to 50:1, |
| Lauric acid:caprylic acid | = | 50:2 to 50:15, |
| Lauric acid:pelargonic acid | = | 50:2 to 50:15, |
| Lauric acid:capric acid | = | 50:2 to 50:15, |
| Lauric acid:myristic acid | = | 50:10 to 50:20 or |
| Lauric acid:stearic acid | = | 50:2 to 50:20, |

wherein if the other fatty acid is solely capric acid and is not caprylic acid, pelargonic acid, capric acid, myristic acid or stearic acid, then the amount of caproic acid in the ratio is greater than zero.

5. A process according to claim 1, wherein the following weight ratios are chosen between lauric acid and at least two other fatty acids, independently of whether more other fatty acids are present:

Lauric acid:caprylic acid:capric acid=50:1:1 to 50:20:20.

6. A process according to claim 1, wherein the following composition of the fatty acid mixtures in each case relative to the total weight of the fatty acid mixture:

| | |
|---|---|
| Lauric acid: | 10–90% by weight |
| Myristic acid: | 13–18% by weight |
| Palmitic acid: | 8–10% by weight |
| Caprylic acid: | 6–9% by weight |
| Capric acid: | 6–10% by weight |
| Stearic acid: | 10–90% by weight |
| Caproic acid: | 0–1% by weight. |

7. A process according to claim 1, wherein the content of GMCy, GMC and mixtures thereof ranges from 0.1–10.00% by weight.

8. A process according to claim 7, wherein the content ranges from 0.5 to 7.5%.

9. A process according to claim 1, wherein the ratio to one another of GMCy, GMC or mixtures thereof on the one hand and the fatty acid mixture on the other hand is chosen from the range of 20:1 to 1:20.

10. A process according to claim 9, wherein the range is from 5:1 to 1:5.

11. A process for controlling external body odors which comprises applying to the external surface of the body a deodorant active composition comprising a mixture of (a) dodecanoic acid (lauric acid)

(b) at least one other fatty acid, selected from the group of unbranched saturated fatty acids having a chain length of $C_{6-20}$, at least one of the other fatty acids having to have a chain length of greater than $C_{12}$, (c) glyceryl monocaprylate and/or glyceryl monocaprate (d) with omission of ethoxylated glyceryl fatty acid esters and propoxylated glyceryl fatty acid esters wherein the pH of said mixture is below 8, said mixture being an effective deodorant active composition.

12. A process according to claim 11, wherein the other fatty acids (b) are chosen from the group consisting of caproic acid (hexanoic acid), caprylic acid (octanoic acid), pelargonic acid (nonanoic acid), capric acid (decanoic acid), myristic acid (tetradecanoic acid), palmitic acid (hexadecanoic acid) and stearic acid (octadecanoic acid).

13. A process according to claim 11, wherein the following weight ratios are chosen between lauric acid and at least one other fatty acid independently of whether more other fatty acids are present, from the group consisting of:

| | | |
|---|---|---|
| Lauric acid:caproic acid | = | 50:0 to 50:5, |
| Lauric acid:caprylic acid | = | 50:1 to 50:20, |
| Lauric acid:pelargonic acid | = | 50:1 to 50:20, |
| Lauric acid:capric acid | = | 50:1 to 50:20, |
| Lauric acid:myristic acid | = | 50:5 to 50:30 or |
| Lauric acid:stearic acid | = | 50:1 to 50:50, |

wherein if the other fatty acid is solely caproic acid and is not caprylic acid, pelargonic acid, capric acid, myristic acid or stearic acid, then the amount of capric acid in the ratio is greater than zero.

14. A process according to claim 11, wherein the following weight ratios are chosen between lauric acid and at least one other fatty acid, independently of whether more other fatty acids are present, from the group consisting of:

| | | |
|---|---|---|
| Lauric acid:caproic acid | = | 50:0 to 50:1, |
| Lauric acid:caprylic acid | = | 50:2 to 50:15, |
| Lauric acid:pelargonic acid | = | 50:2 to 50:15, |
| Lauric acid:capric acid | = | 50:2 to 50:15, |
| Lauric acid:myristic acid | = | 50:10 to 50:20 or |
| Lauric acid:stearic acid | = | 50:2 to 50:20, |

wherein if the other fatty acid is solely caproic acid and is not caprylic acid, pelargonic acid, capric acid, myristic acid or stearic acid, then the amount of caproic acid in the ratio is greater than zero.

15. A process according to claim 11, wherein the following weight ratios are chosen between lauric acid and at least one other fatty acid, independently of whether more other fatty acids are present:

Lauric acid:caprylic acid:capric acid = 50:1:1 to 50:20:20.

16. A process according to claim 11, wherein the following composition of the fatty acid mixtures in each case relative to the total weight of the fatty acid mixture:

| | |
|---|---|
| Lauric acid: | 10–90% by weight |
| Myristic acid: | 13–18% by weight |
| Palmitic acid: | 8–10% by weight |
| Caprylic acid: | 6–9% by weight |
| Capric acid: | 6–10% by weight |
| Stearic acid: | 10–90% by weight |
| Caproic acid: | 0–1% by weight. |

17. A process according to claim 11, wherein a content of GMCy, GMC or mixtures thereof ranges from 0.1 to 10% by relative to the total weight of the respective formulation.

18. A process according to claim 11, wherein the ratio to one other of GMCy, GMC or mixtures thereof on the one hand and the fatty acid mixture on the other hand ranges from 20:1 to 1:20.

19. An active principle for the selective reduction of coryneform bacteria comprising a mixture of (a) dodecanoic acid (lauric acid)

(b) at least one other fatty acid, selected from the group of unbranched saturated fatty acids having a chain length of $C_{6-20}$, at least one of the other fatty acids having to have a chain length of greater than $C_{12}$, (c) at least one of glyceryl monocaprylate or glyceryl monocaprate (d) with omission of ethoxylated glyceryl fatty acid esters and propoxylated glyceryl fatty acid esters wherein the pH of said mixture is below 8, said mixture being an active principle for selectively reducing coryneform bacteria.

20. A deodorant active composition comprising a mixture of (a) dodecanoic acid (lauric acid)

(b) at least one other fatty acid, selected from the group of unbranched saturated fatty acids having a chain length of $C_{6-20}$, at least one of the other fatty acids having to have a chain length of greater than $C_{12}$, (c) glyceryl monocaprylate and/or glyceryl monocaprate (d) with omission of ethoxylated glyceryl fatty acid esters and propoxylated glyceryl fatty acid esters wherein the pH of said mixture is below 8, said mixture being an effective deodorant active composition.

21. A process according to claim 5, wherein the following weight ratios are chosen between lauric acid and at least two other fatty acids, independently of whether more other fatty acids are present:

Lauric acid:caprylic acid:capric acid=50:1:1 to 50:5:5.

22. A process according to claim 15, wherein the following weight ratios are chosen between lauric acid and at least one other fatty acids, independently of whether more other fatty acids are present:

Lauric acid:caprylic acid:capric acid=50:1:1 to 50:5:5.

* * * * *

UNITED STATES PATENT AND TRADEMARK OFFICE

CERTIFICATE OF CORRECTION

PATENT NO. : 5,690,919

DATED : November 25, 1997

INVENTOR(S) : Rockl, et al.

It is certified that error appears in the above-identified patent and that said Letters Patent is hereby corrected as shown below:

Col. 13, line 15 Delete " capric acid " and substitute -- caproic acid --

Col. 13, line 50 Delete " capric acid " and substitute -- caproic acid --

Col. 14, line 52 Delete " capric acid " and substitute -- caproic acid --

Signed and Sealed this

Eighteenth Day of August, 1998

Attest:

BRUCE LEHMAN

Attesting Officer

*Commissioner of Patents and Trademarks*